United States Patent
Kohara et al.

(10) Patent No.: US 8,831,174 B2
(45) Date of Patent: Sep. 9, 2014

(54) X-RAY IMAGING METHOD AND X-RAY IMAGING APPARATUS

(75) Inventors: Naoki Kohara, Utsunomiya (JP); Hidenosuke Itoh, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 255 days.

(21) Appl. No.: 13/521,122

(22) PCT Filed: Jan. 31, 2011

(86) PCT No.: PCT/JP2011/052454
§ 371 (c)(1),
(2), (4) Date: Jul. 9, 2012

(87) PCT Pub. No.: WO2011/102247
PCT Pub. Date: Aug. 25, 2011

(65) Prior Publication Data
US 2012/0281811 A1 Nov. 8, 2012

(30) Foreign Application Priority Data

Feb. 22, 2010 (JP) .................. 2010-035746

(51) Int. Cl.
*G01N 23/04* (2006.01)
*A61B 6/00* (2006.01)
*A61B 6/06* (2006.01)
*G01N 23/20* (2006.01)

(52) U.S. Cl.
CPC . *A61B 6/06* (2013.01); *A61B 6/484* (2013.01); *A61B 6/4092* (2013.01); *A61B 6/4291* (2013.01); *G01N 23/20008* (2013.01)

USPC .......................................... 378/62

(58) Field of Classification Search
USPC ............................ 378/62, 70, 98.8
See application file for complete search history.

(56) References Cited

U.S. PATENT DOCUMENTS

| | | | |
|---|---|---|---|
| 8,411,816 B2* | 4/2013 | Ohara | 378/36 |
| 8,537,966 B2* | 9/2013 | Ouchi et al. | 378/36 |
| 2010/0246765 A1* | 9/2010 | Murakoshi et al. | 378/62 |
| 2012/0281217 A1 | 11/2012 | Ouchi et al. | |

OTHER PUBLICATIONS

Peiping Zhu et al., "Low-Dose, Simple, and Fast Grating-Based X-Ray Phase-Contrast Imaging". Proceedings of the National Academy of Sciences of the United States of America Aug. 3, 2010 LNKD-PubMed:20643971, vol. 107, No. 31, Aug. 3, 2010, pp. 13576-13581, ISSN: 1091-6490.

Liu Xiao-Song et al., "Comparative Analysis of Phase Extraction Methods Based on Phase-Stepping and Shifting Curve in Grating Interferometry", Chinese Physics B, Bristol GB, vol. 19, No. 4, Apr. 1, 2010, pp. 40701-1 to 040701-7, XP020177092, ISSN: 1674-1056.

Chen Bo et al., "Theory and Method of X-Ray Grating Phase Contrast Imaging", Acta Physica Sinica Chinese Physical Society of China, vol. 57, No. 3, Mar. 2008, pp. 1576-1581, ISSN: 1000-3290 (with English Translation).

(Continued)

*Primary Examiner* — Irakli Kiknadze
(74) *Attorney, Agent, or Firm* — Fitzpatrick, Cella, Harper & Scinto

(57) ABSTRACT

There is provided an X-ray imaging method for reducing unnecessary components caused by a transmittance distribution of an object and unevenness in irradiation by a light source and accurately calculating a differential phase at the time of X-ray imaging by SDG.

7 Claims, 6 Drawing Sheets

(56) References Cited

OTHER PUBLICATIONS

International Preliminary Report on Patentablility (Chaper I) along with The Written Opinion of the International Searching Authority issued Aug. 28, 2012 in International Application No. PCT/JP2011/052454, 9 sheets.

Ya. I. Nesterets et al., "Phase-Contrast Imaging Using a Scanning-Double Grating Configuration", Optics Express, vol. 16, No. 8, Apr. 14, 2008, pp. 5849-5867.

* cited by examiner

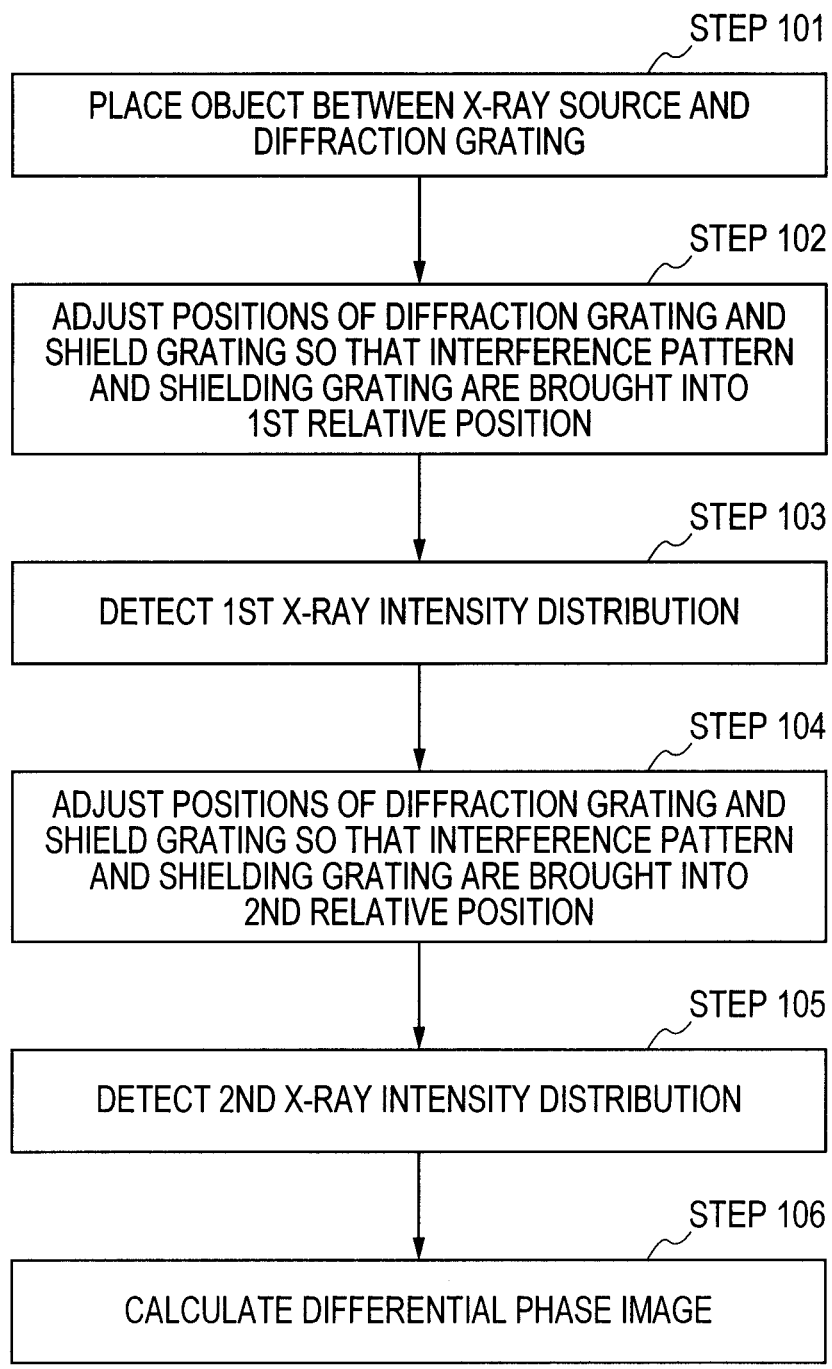

X-RAY IMAGING METHOD AND X-RAY IMAGING APPARATUS

TECHNICAL FIELD

The present invention relates to an X-ray imaging method and an X-ray imaging apparatus.

BACKGROUND ART

An X-ray phase contrast technique is a technique for acquiring a phase image of an object by detecting a phase shift of an X-ray caused by the object.

One of phase contrast techniques, scanning double-grating (hereinafter referred to as SDG) as disclosed in NPL1 has been devised in recent years. SDG uses a diffraction grating which forms a periodic interference intensity distribution (hereinafter referred to as an interference pattern) at a specific distance from the diffraction grating and a shielding grating which is placed at the position where the interference pattern is formed. Detecting an X-ray intensity distribution while simultaneously moving the two gratings enables acquisition of a phase contrast image in one imaging operation.

FIG. 7 illustrates a configuration of an imaging apparatus which performs SDG described above.

The imaging apparatus illustrated in FIG. 7 includes an X-ray source 111 which has spatial coherence on a diffraction grating such that an interference pattern is formed and a diffraction grating 113 for dividing an X-ray applied from the X-ray source 111 into diffracted light components and forming an interference pattern. The imaging apparatus is also provided with a shielding grating 114 including periodically arranged shielding portions blocking an X-ray and transmitting portions transmitting an X-ray, which is placed at a position where an interference pattern is to be formed. The imaging apparatus further includes a detector 115 which detects an intensity distribution of an X-ray transmitted through the shielding grating, a moving unit 116 of the diffraction grating, and a moving unit 117 of the shielding grating. Note that the shielding grating 114 has the same period and the same period direction as the period and the period direction of an interference pattern formed by the diffraction grating 113 when an object is not placed between the X-ray source and the position where the interference pattern is formed.

The principle of SDG will be briefly described. When an X-ray emitted from the X-ray source 111 passes through an object 112, the wavefront of the X-ray has a tilt (hereinafter referred to as a differential phase) corresponding to the refractive index and the shape of the object. When the X-ray having passed through the object is diffracted by the diffraction grating 113, an interference pattern with a distortion corresponding to the differential phase of the object is formed. The process of placing the shielding grating 114 at a position where the interference pattern is formed (hereinafter referred to as a Talbot position) and detecting the X-ray transmitted through the shielding grating 114 by the detector 115 enables detection of distortion in the interference pattern caused by the object as an X-ray intensity distribution. However, since the X-ray is periodically shielded by the shielding grating 114, this process can acquire only part of information on the phase of the object.

Accordingly, the X-ray intensity distribution is detected by moving the diffraction grating 113 and the shielding grating 114 in sync with each other in a direction of the period of the shielding grating by an amount corresponding to one period or more while keeping the relative position between the shielding grating 114 and the interference pattern.

The SDG operation enables acquisition of an image in which an absorption image and a differential phase image of an object are superimposed in one imaging operation.

An X-ray intensity distribution acquired by the method of NPL1, however, includes unnecessary components caused by an X-ray transmittance distribution of an object and unevenness in X-ray irradiation by an X-ray source. Accordingly, the method of NPL1 suffers from the inability to accurately measure the phase distribution of an X-ray having passed through an object.

CITATION LIST

Non Patent Literature

NPL 1: Y. Nesterets and S. Wilkins, "Phase contrast imaging using scanning-double-grating configuration," OPTICS EXPRESS, Vol. 16, No. 8, April 2008

SUMMARY OF INVENTION

The present invention has been made in consideration of the above-described problem, and has as its object to provide an X-ray imaging method and an X-ray imaging apparatus for reducing unnecessary components caused by a transmittance distribution of an object and unevenness in irradiation by a light source at the time of X-ray imaging by SDG and enabling higher-accuracy measurement of a phase distribution.

According to one aspect of the present invention, an X-ray imaging apparatus comprises: a X-ray source; a diffraction grating for diffracting X-ray from the X-ray source to form an interference pattern wherein dark and light portions are arranged; a shielding grating including a shielding portion shielding the X-ray and a transmitting portion transmitting the X-ray; a X-ray detector for detecting an intensity distribution of the X-ray transmitted through the shielding grating; an arithmetic operation unit for deriving a phase information of an object based on a detection result of the X-ray detector; and a moving unit for moving the diffraction grating and the shielding grating, wherein the interference pattern and the diffraction grating are capable of being brought into a first relative position such that the shielding portion of the shielding grating shields a half of the light portion of the interference pattern, and a second relative position such that the relative position between the shielding grating and the interference pattern is shifted from the first position by a width of the shielding portion of the shielding grating, in a direction of a period of the shielding grating, wherein the X-ray detector detects a first X-ray intensity distribution while diffraction grating and the shielding grating are moved by the moving unit in the direction of the period of the shielding grating with keeping the first relative position between the interference pattern and the shielding grating, and a second X-ray intensity distribution while diffraction grating and the shielding grating are moved by the moving unit in the direction of the period of the shielding grating with keeping the second relative position between the interference pattern and the shielding grating, and wherein the arithmetic operation unit calculates a phase information of an object based on the first and second X-ray intensity distributions.

Other aspects of the present invention will become apparent from the following description of the embodiments.

BRIEF DESCRIPTION OF DRAWINGS

FIG. 2 is a flow chart illustrating the procedure of an imaging method according to Example 1 of the present invention.

DESCRIPTION OF EMBODIMENTS

Figure 1:
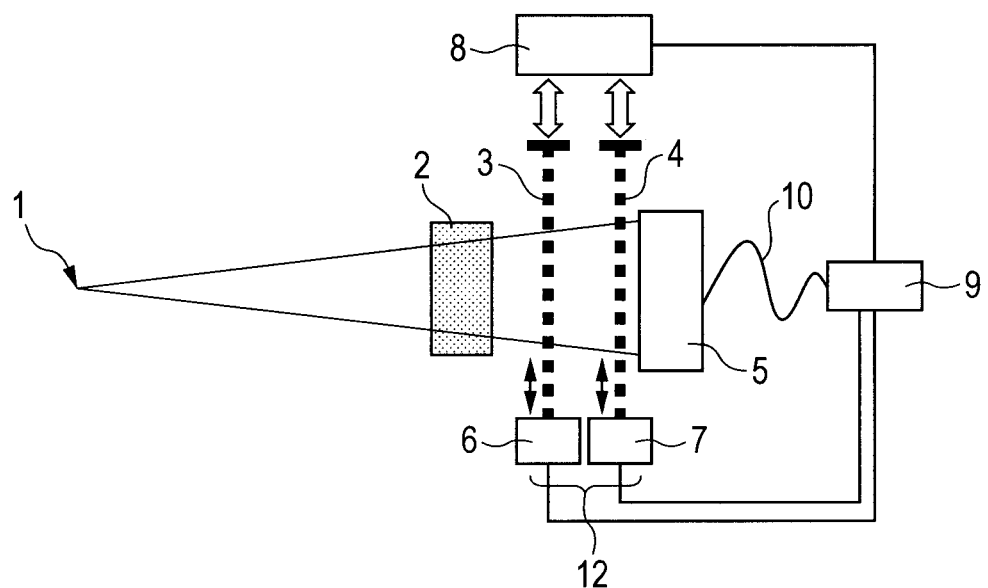
FIG. 1 is a schematic diagram of a configuration of an X-ray imaging apparatus according to an embodiment of the present invention.

An embodiment of the present invention will be described with reference to the accompanying drawings. Note that the same components in the drawings are denoted by the same reference numerals, and a redundant description thereof will be omitted.

FIG. 1 illustrates an X-ray imaging apparatus according to this embodiment. The X-ray imaging apparatus according to this embodiment includes an X-ray source 1 and a diffraction grating 3 which diffracts an X-ray from the X-ray source to form an interference pattern in which dark and light portions are arranged. The X-ray imaging apparatus also includes a shielding grating 4 in which shielding portions blocking an X-ray and transmitting portions transmitting an X-ray are arranged. In the shielding grating 4, the shielding portions and the transmitting portions are arranged in the same period and in the same period direction as the period and the period direction of an interference pattern formed by the diffraction grating 3 when an object is not placed between the X-ray source and a position where the interference pattern is formed. The X-ray imaging apparatus further includes a moving unit 12, which includes a first moving unit 6 for moving the diffraction grating and a second moving unit 7 for moving the shielding grating. The X-ray imaging apparatus further includes a length detector 8 which detects the respective movement amounts of the diffraction grating 3 and the shielding grating 4.

The X-ray imaging apparatus further includes a detector 5 which detects an intensity distribution of an X-ray having passed through the shielding grating 4 and an arithmetic operation device 9 for calculating a differential phase image of an object from a first X-ray intensity distribution and a second X-ray intensity distribution obtained by the detector 5. Note that the first X-ray intensity distribution and the second X-ray intensity distribution will be described later. The arithmetic operation device 9 and the detector 5 are connected by a cable 10. The components will be described below.

An X-ray emitted from the X-ray source 1 is diffracted by the diffraction grating 3, thereby forming an interference pattern. To this end, an X-ray needs to have coherence. The X-ray source 1 is designed such that $\lambda \times (R/s)$ is sufficiently larger than a period d of the diffraction grating 3 (where $\lambda$ is an X-ray wavelength, R is the distance between the X-ray source 1 and the diffraction grating 3, and s is the size of an X-ray generation area of the X-ray source 1).

Although the object 2 is placed between the X-ray source 1 and the diffraction grating 3 in FIG. 1, an object 2 may be placed between the diffraction grating 3 and the shielding grating 4.

The diffraction grating 3 is a one-dimensional phase modulating grating with a periodic structure which periodically modulates the phase of an applied X-ray by one of $\pi$ radians and $\pi/2$ radians. Although a one-dimensional shielding grating which periodically blocks an X-ray may be used instead of the one-dimensional phase modulating grating, the one-dimensional phase modulating grating is more desirable in terms of the dosage of X-rays entering the detector. An interference pattern to be formed by the diffraction grating 3 is formed at a position satisfying Expression 0:

$$\frac{1}{z_0} + \frac{1}{z} = \frac{1}{N}\frac{\lambda}{d^2} \qquad \text{Expression 0}$$

In an interference pattern to be formed in this embodiment, light portions and dark portions of the interference pattern are arranged so as to have widths in the proportion of 1:1. However, the present invention can also be applied to a case where any other interference pattern is formed. Note that the widths of light and dark portions of an interference pattern in this specification each refer to an interference pattern width in a direction of the period of the interference pattern. Also note that a light portion in this specification refers to a portion with a high X-ray intensity while a dark portion refers to a portion with a low X-ray intensity.

In Expression 0, $z_0$ is the distance between the X-ray source 1 and the diffraction grating 3, z is the distance between the diffraction grating 3 and the interference pattern, d is the period of the diffraction grating 3, and $\lambda$ is an X-ray wavelength.

Letting n be a natural number, N is given by (n−½) in the case of a π/2 radian modulation grating, is given by (n/4−⅛) in the case of a n radian modulation grating, and is given by n in the case of a shielding grating.

Note that a substance with high X-ray transmittance such as silicon is preferably used as the material for the diffraction grating 3. In addition, a diffraction grating whose phase modulation amount is one of π radians and π/2 radians is generally used, the diffraction grating used in this embodiment is not limited to this.

The shielding grating 4 is a one-dimensional shielding grating in which shielding portions blocking an X-ray and transmitting portions transmitting an X-ray are arranged in a one-dimensional periodic manner. The period and the period direction of the shielding grating 4 are the same as the period and the period direction of an interference pattern to be formed at a position where the shielding grating 4 is placed by the diffraction grating 3 when an object is not placed between the X-ray source and the shielding grating. Note that the shielding portions of the shielding grating in this specification need not completely block X-rays.

The shielding grating 4 is placed at a position to shield a half of each light portion of an interference pattern when an object is not placed between the X-ray source and the shielding grating. Assume that the relative position between the shielding grating 4 and the interference pattern at this time is a first relative position. If, of the interference pattern and the shielding grating 4 at the first relative position, only the shielding grating 4 is moved in the direction of the period of the shielding grating by the width of each shielding portion, the shielding grating 4 shields a half of each light portion of the interference pattern when the object is not placed between the X-ray source and the shielding grating. The light portion of the interference pattern shielded by the shielding grating 4 at this time is a light portion passing through the shielding grating when the interference pattern and the shielding grating 4 are at the first relative position. Assume that the relative position between the shielding grating 4 and the diffraction grating 3 at the time is a second relative position. Note that the position of the shielding grating 4 is adjusted to suit the position of the interference pattern in this embodiment, the position of the interference pattern may be adjusted to suit the position of the shielding grating 4. The position of the diffraction grating 3 may be adjusted in order to adjust the position of the interference pattern. Although the proportion of the width of each shielding portion to the width of each transmitting portion in the direction of the period of the shielding grating 4 is 1:1 in this embodiment, the proportion may be set to any other value depending on the proportion of the width of each light portion of the interference pattern to the width of each dark portion.

In other words, it suffices that the shielding grating shields a half of each light portion of the interference pattern and transmits the other half of the light portion and that the relative position between the shielding grating and the interference pattern can switch between the first relative position and the second relative position.

The moving unit 12 according to this embodiment includes the first moving unit 6 and the second moving unit 7, and the first moving unit 6 and the second moving unit 7 move the diffraction grating 3 and the shielding grating 4, respectively, in the direction of the period of the shielding grating. The first moving unit 6 and the second moving unit 7 can move the diffraction grating 3 and the shielding grating 4 while keeping the relative position between the shielding grating 4 and the interference pattern at the first relative position or the second relative position.

In order to move the diffraction grating 3 and the shielding grating 4 while keeping the relative position between the interference pattern and the shielding grating 4, the ratio between a distance by which the diffraction grating moves and a distance by which the shielding grating moves may be set to the ratio between the distance between the X-ray source and the diffraction grating and the distance between the X-ray source and the shielding grating when imaging is to be performed using divergent X-rays.

On the other hand, when imaging is to be performed using parallel X-rays, the diffraction grating and the shielding grating can be moved in the direction of the period of the shielding grating while keeping the relative position between the interference pattern and the shielding grating by making the distance by which the diffraction grating moves equal to the distance by which the shielding grating moves.

The moving unit need not include the first moving unit and the second moving unit, and the diffraction grating 3 and the shielding grating 4 may be moved by one moving unit. Each moving unit is driven by a motor or a piezoelectric actuator.

The length detector 8 is a device for detecting displacements of the diffraction grating 3 and the shielding grating 4 in the respective movement directions, i.e., movement amounts and is installed as needed.

The detector 5 detects an intensity distribution of X-rays having passed through the shielding grating 4 when the diffraction grating 3 and the shielding grating 4 are moving in the direction of the period of the shielding grating while keeping the first relative position between the interference pattern and the shielding grating 4. After that, the detector 5 similarly detects an intensity distribution of X-rays having passed through the shielding grating 4 when the diffraction grating 3 and the shielding grating 4 are moving in the direction of the period of the shielding grating while keeping the second relative position between the interference pattern and the shielding grating 4.

In this specification, an X-ray intensity distribution detected when the diffraction grating and the shielding grating are moving while keeping the first relative position will be referred to as a first X-ray intensity distribution while an X-ray intensity distribution detected when the diffraction grating and the shielding grating are moving while keeping the second relative position will be referred to as a second X-ray intensity distribution.

That is, when an object is not placed between the X-ray source and the diffraction grating or between the diffraction grating and the shielding grating, a half of each light portion of the interference pattern is shielded at the time of imaging of the first X-ray intensity distribution, and the other half of each light portion of the interference pattern is shielded at the time of imaging of the second X-ray intensity distribution. Note that when an object is placed between the X-ray source and the diffraction grating or between the diffraction grating and the shielding grating, and there is a differential phase, the interference pattern changes its position in the period direction depending on the differential phase.

A distance by which the shielding grating 4 moves when the first X-ray intensity distribution and the second X-ray intensity distribution are detected is a natural number multiple of the period of the shielding grating 4 or sufficiently longer than the period of the shielding grating 4. By this means, pixels of the detector acquire the first X-ray intensity distribution and the second X-ray intensity distribution with phase contract information.

An arithmetic operation unit of the arithmetic operation device performs calculation using the acquired first X-ray intensity distribution and second X-ray intensity distribution, and a differential phase of an object can be obtained.

The detector 5 includes an image pickup element capable of detecting X-rays. For example, an image pickup element of a type which converts an X-ray into visible light by a phosphor and then detects the visible light by a CCD element or a CMOS element can be used as the image pickup element.

The arithmetic operation device 9 is connected to the detector 5 through the cable 10 and includes a control unit, a storage unit (memory), the arithmetic operation unit, and a display unit (not shown).

The control unit controls the operation of the moving unit based on movement amounts of the diffraction grating 3 and the shielding grating 4 detected by the length detector 8 to move the diffraction grating 3 and the shielding grating 4. Even in the absence of the length detector 8, movement of the diffraction grating 3 and the shielding grating 4 can be appropriately performed by storing and calculating amounts of movement by the moving unit. The appropriate movement in this case refers to moving the diffraction grating 3 and the shielding grating 4 in the direction of the period of the shielding grating while keeping the relative position between the interference pattern and the shielding grating 4 at the first relative position or the second relative position.

The storage unit stores an X-ray intensity distribution acquired by the detector 5.

The arithmetic operation unit calculates a differential phase from an X-ray intensity distribution stored in the storage unit. The arithmetic operation unit also calculates a phase image of an object as needed. A calculation method will be described below.

The first X-ray intensity distribution and the second X-ray intensity distribution acquired by the detector 5 each include not only a differential phase but also errors caused by a transmittance distribution and unevenness in irradiation by the light source. In order to reduce such errors, a differential phase is calculated based on the first X-ray intensity distribution and the second X-ray intensity distribution.

If each intensity in a first X-ray intensity distribution IA increases by a positive differential phase, as indicated by (Expression 1) below, each intensity in a second X-ray intensity distribution IB decreases by the same magnitude, as indicated by (Expression 2) below. Note that a half of each light portion need not be an exact half and refers to a half within tolerance.

$$I_A(x, y) = \frac{I_0(x, y)}{2}\left(1 + a\frac{\partial \Phi(x, y)}{\partial x}\right) \quad \text{Expression 1}$$

$$I_B(x, y) = \frac{I_0(x, y)}{2}\left(1 - a\frac{\partial \Phi(x, y)}{\partial x}\right) \quad \text{Expression 2}$$

In (Expression 1) and (Expression 2), $\Phi$ is an X-ray phase distribution immediately in front of the diffraction grating, x is a coordinate in a direction of the period of the diffraction grating within a diffraction grating plane, and y is a coordinate in a direction orthogonal to the period direction.

In the expressions, $I_0$ is an X-ray intensity distribution acquired without a diffraction grating and a shielding grating, i.e., an X-ray intensity including effects of a transmittance distribution and unevenness in irradiation by the light source when there is no differential phase.

An intensity distribution proportional to a differential phase at all pixels is obtained by dividing phase contrast information that is the difference between the first and second X-ray intensity distributions by the sum $I_0$ that is the sum of the first and second X-ray intensity distributions, as indicated by (Expression 3) below.

$$a\frac{\partial \Phi(x, y)}{\partial x} = \frac{I_A - I_B}{I_A + I_B} \quad \text{Expression 3}$$

In order to calculate a differential phase in terms of radians, the intensity distribution indicated by (Expression 3) above that is obtained by dividing the difference between the first and second X-ray intensity distributions by the sum of the first and second X-ray intensity distributions may be multiplied by a coefficient of 1/a determined by the period of the diffraction grating and the distance between the diffraction grating and the shielding grating. The coefficient can be derived from the consideration below. Letting θ be the difference between an angle of the position of the interference pattern viewed from the diffraction grating when there is a differential phase and an angle of the position of the interference pattern when there is no differential phase (i.e., an angle by which the position of the interference pattern is shifted by an object), θ is given by (Expression 4) below. This indicates that the interference pattern is formed in a direction to normal to the equiphase surface.

$$\theta(x, y) = \frac{\lambda}{2\pi} \frac{\partial \Phi(x, y)}{\partial x} \quad \text{Expression 4}$$

Since the rate of change in X-ray intensity caused by a shift in the position of the interference pattern is the ratio of a shift z·tan θ in the position of the interference pattern to a width p/4 of a part of the interference pattern shielded by a second diffraction grating, (Expression 5) is derived.

$$a\frac{\partial \Phi(x, y)}{\partial x} = \frac{z\tan\theta(x, y)}{p/4} \approx \frac{4z\theta(x, y)}{p} \quad \text{Expression 5}$$

In (Expression 5), z is the distance between the diffraction grating 3 and the shielding grating 4. Note that the distance between the center of the diffraction grating and the center of the shielding grating is assumed to be the distance between the diffraction grating and the shielding grating in this specification. From (Expression 4) and (Expression 5), the coefficient of 1/a is as given by (Expression 6) below.

$$\frac{1}{a} \approx \frac{\pi p}{2z\lambda} \quad \text{Expression 6}$$

Although (Expression 5) is based on the assumption that a shift in the position of the interference pattern derived from X-rays is small, more accurate calculation of a differential phase by exactly solving (Expression 3) to (Expression 5) can be easily performed.

The arithmetic operation unit calculates a differential phase of an object by using the first X-ray intensity distribution and the second X-ray intensity distribution detected by the detector and the calculation method described above.

The display unit displays an image based on an X-ray intensity distribution acquired by the detector or a calculation result obtained by the arithmetic operation unit.

The arithmetic operation unit may calculate a phase distribution from differential phases obtained by changing directions of the diffraction grating 3 and the shielding grating 4 by the same amount. The phase distribution may be displayed by the display unit.

Examples of the present invention will be described below. The present invention, however, is not limited to the examples below.

Example 1

An X-ray imaging apparatus to which the present invention is applied will be described as Example 1.

A configuration of the X-ray imaging apparatus is basically the same as the configuration of the X-ray imaging apparatus described with reference to FIG. 1.

A microfocus X-ray tube with a molybdenum target is used as an X-ray source according to this example. The distance between the X-ray source and a diffraction grating is 1000 mm.

A diffraction grating 31 is a one-dimensional phase modulating grating which modulates the phase of an X-ray having energy of 17.5 keV (whose center wavelength is 0.071 nm) with a period of 6.0 μm by π/2. The diffraction grating 31 is formed of silicon whose thickness changes periodically and is placed at a position to which X-rays generated by the X-ray source are applied. When the X-ray source and the diffraction grating 31 described above are used, since a Talbot position is calculated to be 340 mm (N=½) from (Expression 0), a shielding grating 41 is placed at a distance of 340 mm from the diffraction grating. A one-dimensional shielding grating formed such that a recessed portion with a depth of 20.0 μm and a period of 8.04 μm is filled with gold plating in a silicon substrate and designed to periodically block X-rays having energy of 17.5 keV is used as the shielding grating.

A detector used is a two-dimensional detector which converts an X-ray into visible light by a phosphor and then detects the visible light by a CCD and is placed as close to the shielding grating as possible.

The procedure of an imaging method using the X-ray imaging apparatus according to this example will be described with reference to the flow chart illustrated in FIG. 2.

First, an object is placed between the X-ray source and the diffraction grating (step 101).

The object may be placed between the diffraction grating and the shielding grating instead. In this case, a differential phase of an X-ray having passed through the object is calculated by using z in (Expression 6) as the distance between the object and the shielding grating. The positions of the diffraction grating and the shielding grating are adjusted by a moving unit such that the relative position between an interference pattern and the shielding grating is set to a first relative position (step 102). The relative position between the interference pattern and the shielding grating may be adjusted by adjusting the position of one of the diffraction grating and the shielding grating.

The diffraction grating and the shielding grating are moved independently of and in sync with each other while the relative position between the interference pattern and the shielding grating is kept at the first relative position. In the meantime, a first X-ray intensity distribution is acquired by the detector (step 103). In step 103, a control unit of an arithmetic operation device controls the moving unit according to a detection result obtained by a length detector such that the ratio between a distance by which the diffraction grating moves and a distance by which the shielding grating moves in a direction of the period of the shielding grating is the ratio between the distance between the X-ray source and the diffraction grating and the X-ray source and the shielding grating. An amount by which the shielding grating moves during detection of the first X-ray intensity distribution is equal to one period of the shielding grating.

The positions of the diffraction grating and the shielding grating are adjusted such that the relative position between the interference pattern and the shielding grating is set to a second position (step 104). After that, like step 103, the diffraction grating and the shielding grating are moved independently of and in sync with each other while the relative position between the interference pattern and the shielding grating is kept at the second relative position. In the meantime, a second X-ray intensity distribution is detected (step 105).

An arithmetic operation unit of the arithmetic operation device calculates a differential phase image obtained by dividing the difference between the first X-ray intensity distribution and the second X-ray intensity distribution by the sum of the first X-ray intensity distribution and the second X-ray intensity distribution and then multiplying the quotient by a coefficient represented by (Expression 6) (step 106).

The calculated differential phase image is displayed by a display unit of the arithmetic operation unit 9.

Figure 3A:
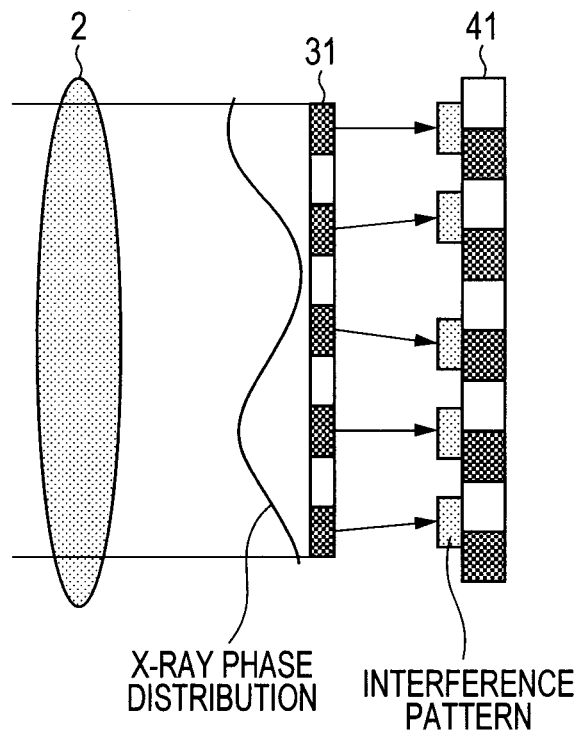
FIG. 3A is a schematic view illustrating a relative position between an interference pattern and a diffraction grating and a shielding grating at the time of acquiring a first X-ray intensity distribution according to Example 1 of the present invention.
Figure 3B:
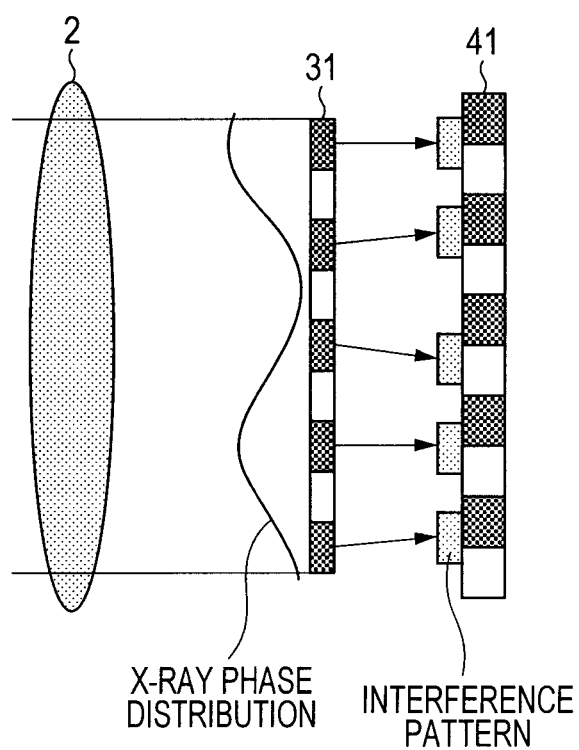
FIG. 3B is a schematic view illustrating a relative position between an interference pattern and the diffraction grating and the shielding grating at the time of acquiring a second X-ray intensity distribution according to Example 1 of the present invention.

FIGS. 3A and 3B illustrate the relative positions among the diffraction grating 31, the interference pattern, and the shielding grating 41 when the relative position between the interference pattern and the shielding grating is set at the first relative position and when the relative position between the interference pattern and the shielding grating is set at the second relative position.

FIG. 3A is a view illustrating the relative position between the diffraction grating 31 and the shielding grating 41 when the interference pattern and the shielding grating 41 are brought into the first relative position.

FIG. 3B is a view illustrating the relative position between the diffraction grating 31 and the shielding grating 41 when the interference pattern and the shielding grating 41 are brought into the second relative position.

As illustrated in FIGS. 3A and 3B, if an object is placed between the X-ray source and the diffraction grating, an interference pattern affected by an X-ray differential phase caused by the object is formed.

Figure 4:
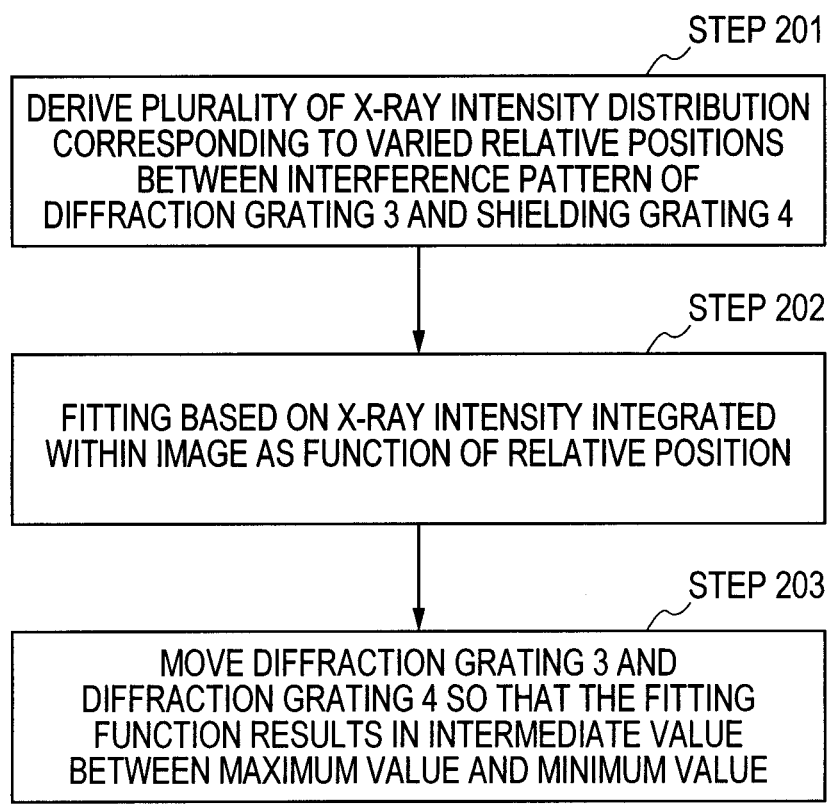
FIG. 4 is a flow chart illustrating the procedure for determining the position of the diffraction grating according to Example 1 of the present invention.

FIG. 4 illustrates an example of the alignment procedure for placing the diffraction grating and the shielding grating such that an interference pattern and the shielding grating are brought into the first relative position or the second relative position.

The alignment procedure in FIG. 4 utilizes a change in the intensity of an X-ray entering the detector caused by a difference in the relative position between the interference pattern and the shielding grating.

It can readily be seen that if the relative position between the interference pattern and the shielding grating is changed, the width of a part of the interference pattern passing through the shielding grating varies between 0 and ½ the period of the shielding grating, and the intensity of an X-ray entering the detector changes.

The first relative position and the second relative position are each a relative position between an interference pattern and the shielding grating when the varying X-ray intensity takes an intermediate value.

The alignment procedure used in the X-ray imaging apparatus according to this example will be described with reference to the flow chart illustrated in FIG. 4. When imaging of an object is to be performed using the X-ray imaging apparatus according to this example, a plurality of X-ray intensity distributions is first detected while the relative position between the interference pattern and the shielding grating is changed (e.g., only the position of the shielding grating is changed) without the object (step 201).

During the detection of each X-ray intensity distribution in step 201, the diffraction grating and the shielding grating may be moved in sync with each other such that the relative position between the interference pattern formed by the diffraction grating and the shielding grating is not changed or may be frozen.

In step 202, fitting is performed based on an X-ray intensity calculated by integrating each X-ray intensity distribution within a detected image as a function of relative position. For example, fitting is performed based on the X-ray intensity as a triangular wave or a sine function using the grating period of the shielding grating as a period.

In step 203, a position where the fitting function takes an intermediate value between the maximum value and the minimum value is calculated, and the diffraction grating and the shielding grating are placed at the position. When the diffraction grating and the shielding grating are placed at this position, the relative position between the interference pattern and the shielding grating is set to the first relative position.

The alignment procedure illustrated in FIG. 4 need not be performed for each imaging operation. The diffraction grating and the shielding grating may be placed at positions obtained by a previous alignment operation.

FIGS. 5A to 5F are charts illustrating results of the imaging simulation about the X-ray imaging apparatus according to this example.

Figure 5A:
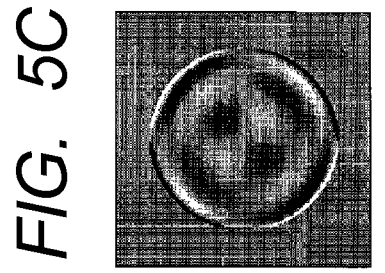
FIG. 5A is a chart illustrating an X-ray intensity distribution on the diffraction grating used on the imaging simulation about the X-ray imaging apparatus according to Example 1 of the present invention.

FIG. 5A is a chart illustrating an X-ray intensity distribution on the diffraction grating caused by a transmittance distribution of an object and unevenness in irradiation by the X-ray source.

Figure 5B:
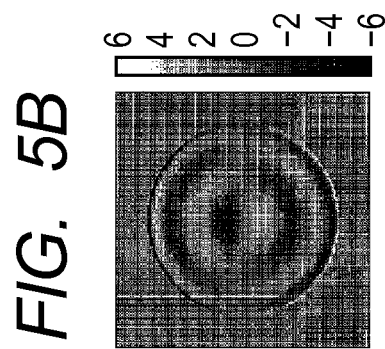
FIG. 5B is a chart illustrating an X-ray phase distribution on the diffraction grating used on the imaging simulation about the X-ray imaging apparatus according to Example 1 of the present invention.

FIG. 5B is an X-ray phase distribution on the diffraction grating caused by the object.

Figure 5C:
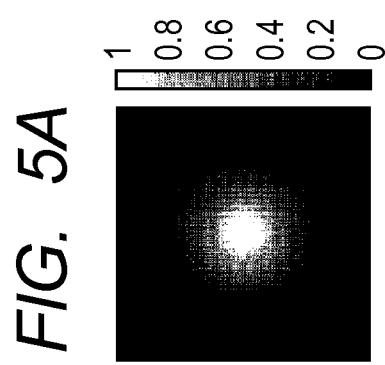
FIG. 5C is a chart obtained by differentiating the X-ray phase distribution in FIG. 5B in a direction of the period of the shielding grating according to Example 1 of the present invention.

FIG. 5C illustrates a differential phase obtained by differentiation of the X-ray phase distribution in FIG. 5B in the direction of the period of the diffraction grating and is a phase contrast image to be acquired by the X-ray imaging method according to this example.

Figure 5D:
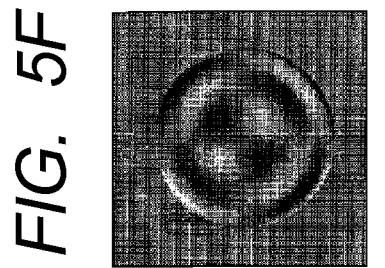
FIG. 5D is a chart illustrating a first X-ray intensity distribution on the diffraction grating calculated from the imaging simulation about the X-ray imaging apparatus according to Example 1 of the present invention.

FIG. 5D is a first X-ray intensity distribution calculated by light wave propagation using the X-ray intensity distribution and the phase distribution illustrated in FIGS. 5A and 5B.

Figure 5E:
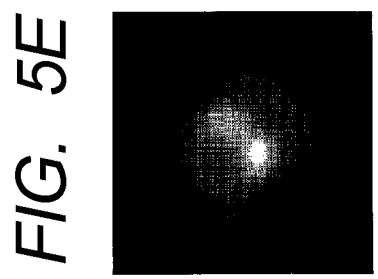
FIG. 5E is a chart illustrating a second X-ray intensity distribution on the diffraction grating calculated from the imaging simulation about the X-ray imaging apparatus according to Example 1 of the present invention.

FIG. 5E is a second X-ray intensity distribution calculated by light wave propagation using the X-ray intensity distribution and the phase distribution illustrated in FIGS. 5A and 5B.

Figure 5F:
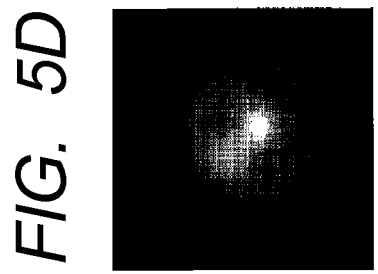
FIG. 5F is a chart illustrating a differential phase image of the object calculated from the imaging simulation about the X-ray imaging apparatus according to Example 1 of the present invention.

FIG. 5F is a differential phase image calculated from FIGS. 5D and 5E and acquired by the X-ray imaging method according to this example.

FIG. 5F and FIG. 5C substantially coincides with each other. This indicates that a phase contrast image with few errors can be obtained by imaging using the X-ray imaging apparatus according to this example.

Example 2

A configuration different from the configuration of Example 1 will be described as Example 2.

Figure 6:
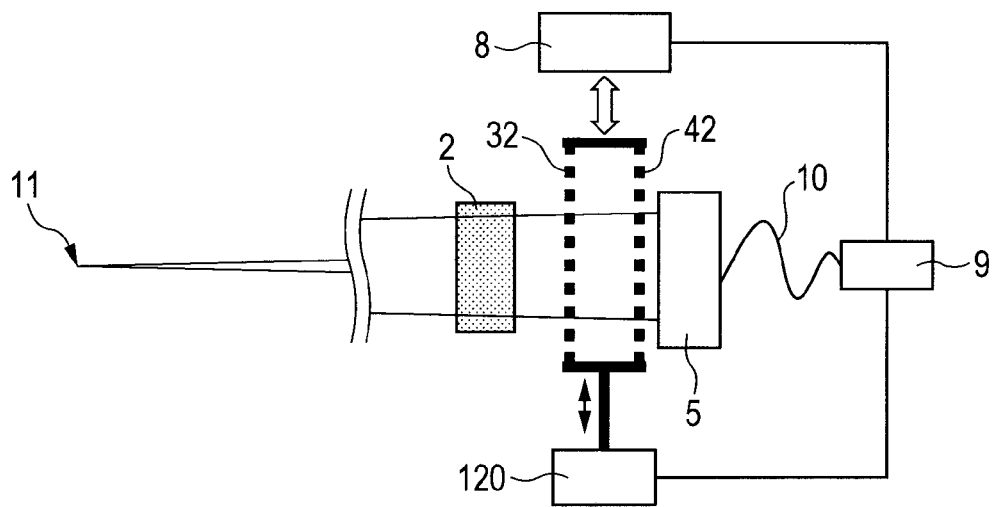
FIG. 6 is a schematic diagram illustrating a configuration of an X-ray imaging apparatus according to Example 2 of the present invention.
Figure 7:
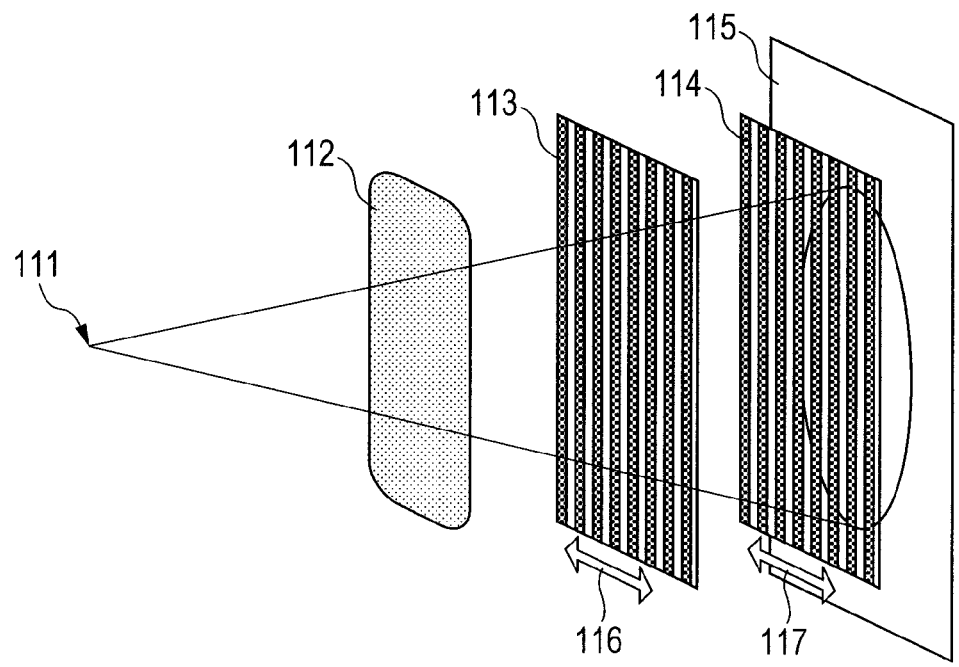
FIG. 7 is a schematic diagram illustrating the configuration of a conventional X-ray imaging apparatus based on SDG.

FIG. 6 illustrates an X-ray imaging apparatus used in this example. Only a difference from Example 1 will be described.

In this example, the distance between an X-ray source 11 and a diffraction grating 32 is increased. With this configuration, substantially parallel X-rays are applied to a diffraction grating 32.

Accordingly, when the diffraction grating 32 and a shielding grating 42 are to be moved while the relative position between an interference pattern to be formed by the diffraction grating and the shielding grating, the diffraction grating 32 and the shielding grating 42 can be moved by a moving unit 120 while the diffraction grating 32 and the shielding grating 42 are fixed.

Since the X-ray source needs to have high intensity and a small radiation angle in this example, synchrotron radiation having energy of 17.7 keV is used in the X-ray source 11. The diffraction grating 32 is placed in an experimental hutch at a distance of 150 m from the X-ray source 11. The diffraction grating 32 is a one-dimensional phase modulating grating which modulates the phase of an X-ray having energy of 17.7 keV with a period of 6.0 µm by n/2. Since a Talbot position is calculated to be 257 mm (N=½) from (Expression 0), the shielding grating 42 is fixed to a plate-like member at a distance of 257 mm from the diffraction grating 32. The shielding grating 42 has the same period of 6.0 µm as the period of the diffraction grating 32 and is a one-dimensional shielding grating which periodically blocks an X-ray having energy of 17.7 keV.

When the relative position between the diffraction grating 32 and the shielding grating 42 is fixed, alignment (an example of which is illustrated in FIG. 4) is performed to fix the relative position.

The diffraction grating 32 and the shielding grating 42 are placed such that an interference pattern and the shielding grating 42 are brought into a first relative position. The relative position between the diffraction grating 32 and the shielding grating 42 are fixed at this position. After a first X-ray intensity distribution is detected as in Example 1, one of the diffraction grating 32 and the shielding grating 42 is shifted by the width of a shielding portion of the shielding grating in a direction of the period. The relative position between the diffraction grating 32 and the shielding grating 42 is fixed again. After a second X-ray intensity distribution is detected as in Example 1, a differential phase image is calculated by an arithmetic operation unit, and the differential phase image is displayed by a display unit.

REFERENCE SIGNS LIST

1: X-ray source
3: diffraction grating
4: shielding grating
5: detector
12: moving unit
9: arithmetic operation unit

INDUSTRIAL APPLICABILITY

The present invention can be used in an object imaging apparatus which uses a phase change caused when an X-ray passes through an object.

This application claims the benefit of Japanese Patent Application No. 2010-035746, filed Feb. 22, 2010, which is hereby incorporated by reference herein in its entirety.

The invention claimed is:

1. An X-ray imaging apparatus comprising:
   a diffraction grating for diffracting X-rays from an X-ray source to form an interference pattern wherein dark and light portions are arranged;
   a shielding grating including a shielding portion shielding a part of the X-rays forming the interference pattern and a transmitting portion transmitting a part of the X-rays forming the interference pattern;

an X-ray detector for detecting an intensity distribution of the X-rays transmitted through the shielding grating;

an arithmetic operation unit for deriving a phase information of an object based on a detection result of the X-ray detector; and a moving unit for moving the diffraction grating and the shielding grating, wherein the interference pattern and the diffraction grating are capable of being brought into a first relative position such that the shielding portion of the shielding grating shields a half of the light portion of the interference pattern, and a second relative position such that the relative position between the shielding grating and the interference pattern is shifted from the first position by a width of the shielding portion of the shielding grating, in a direction of a period of the shielding grating, wherein the X-ray detector detects a first X-ray intensity distribution while diffraction grating and the shielding grating are moved by the moving unit in the direction of the period of the shielding grating with keeping the first relative position between the interference pattern and the shielding grating, and a second X-ray intensity distribution while diffraction grating and the shielding grating are moved by the moving unit in the direction of the period of the shielding grating with keeping the second relative position between the interference pattern and the shielding grating, and wherein the arithmetic operation unit calculates a phase information of an object based on the first and second X-ray intensity distributions.

2. The X-ray imaging apparatus according to claim 1, wherein the dark and light portions of the interference pattern are arranged in a constant period, and the shielding portion and the transmitting portion of the shielding grating are arranged in the same period and in the same period direction as those of the interference pattern.

3. The X-ray imaging apparatus according to claim 1, wherein the arithmetic operation unit calculates the phase information of the object by dividing a difference between the first and second X-ray intensity distributions by a sum of the first and second X-ray intensity distributions, and thereafter multiplying a result of the division by a factor determined based on the period of the diffraction grating and a distance between the diffraction grating and the shielding grating.

4. The X-ray imaging apparatus according to claim 1, wherein the first relative position is defined such that, when an integral intensity of the X-rays is calculated based on the detection of the intensity distribution of the X-rays one relative position by one relative position for a plurality of relative positions between the interference pattern and the shielding grating while changing the relative position between the interference pattern and the shielding grating, the integral intensity of the X-rays calculated for the first relative position is an intermediate value between a maximum value and a minimum value among the integral intensities of the X-rays calculated for the plurality of relative positions.

5. The X-ray imaging apparatus according to claim 1, wherein the moving unit includes a first moving device for moving the diffraction grating and a second moving device for the shielding grating.

6. An X-ray imaging method using an X-ray imaging apparatus that comprises an X-ray source, a diffraction grating for diffracting X-rays from the X-ray source to form an interference pattern wherein dark and light portions are arranged, a shielding grating including a shielding portion shielding the X-rays and a transmitting portion transmitting the X-rays an X-ray detector for detecting an intensity distribution of the X-rays transmitted through the shielding grating, an arithmetic operation unit for deriving a phase information of an object based on a detection result of the X-ray detector, and a moving unit for moving the diffraction grating and the shielding grating, wherein the imaging method comprising steps of:

moving the diffraction grating and/or the shielding grating, to be brought into a first relative position such that the shielding portion of the shielding grating shields a half of the light portion of the interference pattern;

detecting by the X-ray detector a first X-ray intensity distribution while diffraction grating and the shielding grating are moved by the moving unit in the direction of the period of the shielding grating with keeping the first relative position between the interference pattern and the shielding grating;

moving the diffraction grating and/or the shielding grating, to be brought into a second relative position such that the relative position between the shielding grating and the interference pattern is shifted from the first position by a width of the shielding portion of the shielding grating, in a direction of a period of the shielding grating;

detecting by the X-ray detector a second X-ray intensity distribution while diffraction grating and the shielding grating are moved by the moving unit in the direction of the period of the shielding grating with keeping the second relative position between the interference pattern and the shielding grating, and calculating, by the arithmetic operation unit, a phase information of an object based on the first and second X-ray intensity distributions.

7. An X-ray imaging system comprising:

an X-ray source;

a diffraction grating for diffracting X-rays from the X-ray source to form an interference pattern wherein dark and light portions are arranged;

a shielding grating including a shielding portion shielding a part of the X-rays forming the interference pattern and a transmitting portion transmitting a part of the X-rays forming the interference pattern;

an X-ray detector for detecting an intensity distribution of the X-rays transmitted through the shielding grating;

an arithmetic operation unit for deriving a phase information of an object based on a detection result of the X-ray detector;

a moving unit for moving the diffraction grating and the shielding grating; and a display unit for displaying an image based on the X-ray intensity distribution acquired by the detector or the phase information of an object, wherein the interference pattern and the diffraction grating are capable of being brought into a first relative position such that the shielding portion of the shielding grating shields a half of the light portion of the interference pattern, and a second relative position such that the relative position between the shielding grating and the interference pattern is shifted from the first position by a width of the shielding portion of the shielding grating, in a direction of a period of the shielding grating, wherein the X-ray detector detects a first X-ray intensity distribution while diffraction grating and the shielding grating are moved by the moving unit in the direction of the period of the shielding grating with keeping the first relative position between the interference pattern and the shielding grating, and
a second X-ray intensity distribution while diffraction grating and the shielding grating are moved by the moving unit in the direction of the period of the shielding grating with keeping the second relative position between the interference pattern and the shielding grating, and
wherein the arithmetic operation unit calculates a phase information of an object based on the first and second X-ray intensity distributions.

* * * * *